United States Patent [19]

Umemura et al.

[11] Patent Number: 4,552,703
[45] Date of Patent: Nov. 12, 1985

[54] PRODUCTION OF OPTICALLY ACTIVE CYCLOPENTENOLONES

[75] Inventors: Takeaki Umemura; Ayumu Inoue; Satoshi Mitsuda, all of Osaka, Japan

[73] Assignee: Sumitomo Chemical Company, Limited, Osaka, Japan

[21] Appl. No.: 600,389

[22] Filed: Apr. 16, 1984

[30] Foreign Application Priority Data

Apr. 19, 1983 [JP] Japan .................... 58-069568
Apr. 19, 1983 [JP] Japan .................... 58-069569

[51] Int. Cl.$^4$ .................... C07C 77/00; C07C 45/65
[52] U.S. Cl. .................... 260/466; 260/467; 568/351
[58] Field of Search ........... 568/347, 351; 260/466, 260/467

[56] References Cited

U.S. PATENT DOCUMENTS

| | | | |
|---|---|---|---|
| 3,009,944 | 11/1961 | Brunnberg | 260/467 |
| 3,189,654 | 6/1965 | Arthur | 568/351 |
| 4,000,179 | 12/1976 | Ayerst | 260/466 |
| 4,205,008 | 5/1980 | Martel et al. | 260/456 R |
| 4,385,186 | 5/1983 | Matsuo et al. | 568/379 |

FOREIGN PATENT DOCUMENTS 58-47495 3/1983 Japan .................... 568/379

OTHER PUBLICATIONS

McOmie, "Protective Groups in Organic Chemistry", Plenum Press, pp. 119–120, (1973).
Baker et al., J. Chem. Soc., 1952, pp. 1193–1207.
Bordwell et al., J. A. C. S., vol. 82, pp. 3588–3598, (1960).
Shin et al., Bull. Chem. Jap. Soc., vol. 43, pp. 3219–3223, (1970).

*Primary Examiner*—James H. Reamer
*Attorney, Agent, or Firm*—Cushman, Darby & Cushman

[57] ABSTRACT

Optically active cyclopentenolones, useful as an intermediate to be directed to pyrethroid insecticide, are produced starting from the optically active cyclopentenolones with the opposite configuration, through the formation of their nitrate ester, followed by the hydrolysis with inversion of configuration.

13 Claims, No Drawings

PRODUCTION OF OPTICALLY ACTIVE CYCLOPENTENOLONES

GENERAL STATEMENT OF THE INVENTION

This invention relates to the production of optically active cyclopentenolones, useful as the intermediates to be directed to pyrethroid insecticides. In particular, this invention relates to the production of optically active cyclopentenolones denoted as compounds of the formula (I):

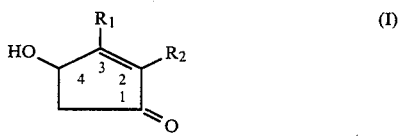

wherein $R_1$ is a hydrogen atom or a $C_1$–$C_3$ alkyl group, and $R_2$ is a $C_1$–$C_6$ alkyl, $C_2$–$C_6$ alkenyl or $C_2$–$C_6$ alkynyl group, from the optically active cyclopentenolones of the formula (I) having the opposite configuration, through the formation of their nitrate ester, followed by the hydrolysis with an inversion of configuration.

The nitrate esters of the cyclopentenolones are newly synthesized compounds, and are denoted as compounds of the formula (II):

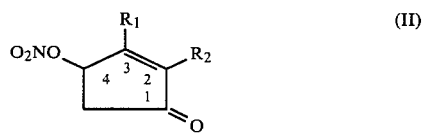

wherein $R_1$ and $R_2$ are the same as defined in the formula (I).

Accordingly, the present invention relates to a method of the production of optically active cyclopentenolones of the formula (I), which comprises hydrolyzing nitrate ester of an optically active cyclopentenolone of the formula (II) in neutral or acidic medium, with the inversion of configuration at the asymmetric center of the 4-position to obtain the configurationally inverted cyclopentenolone of the formula (I).

It has been known that the cyclopentenolones, the compounds (I) above, are serving as the important alcoholic moieties in a series of the carboxylate esters, commonly called synthetic pyrethroids which have been well reputed for their excellent insecticidal activities. Because of existence of an asymmetric carbon atom at the 4-position, two optical isomers, which are antipodal each other, are present in the cyclopentenolone molecule.

Further, it has been known that, in general, the optically active cyclopentenolones having (S)-configuration become to the esters with greater insecticidal activity than the corresponding esters of the racemic cyclopentenolones or the cyclopentenolones having (R)-configuration by the reaction of the esterification with cyclopropane carboxylic acids. See, for example, a report by Matsuo, et al, Pestic, Sci, 11, 202 (1980).

Therefore, there has been desired the development of an economical, convenient method for producing the compounds (I) consisting predominantly of (S)-isomer thereof.

Some methods have been known hitherto: for instance; U.S. Pat. No. 4,385,186 describes a method of the chemical optical resolution in which the racemic cyclopentenolone is converted to the corresponding acid phthalate, and then resolved with an optically active amine; and Japanese Unexamined Patent Publication Sho No. 58 (1983)-47495 describes a method of the biochemical optical resolution in which the racemic cyclopentenolone is converted to an organic carboxylic acid ester thereof, and then the asymmetric hydrolysis is effected microbiologically using an esterase.

Although these methods yield the aimed (S)-isomer of cyclopentenolone, they yield at the same time an almost equal amount of the unwanted antipode thereof as the byproduct, in other words, the cyclopentenolone consisting of, or rich in, the (R)-isomer.

As mentioned before, the cyclopentenolone consisting of, or rich in, the (R)-isomer is inferior, with respect to the insecticidal activity, to the corresponding (S)-isomer, or (S)-isomer-rich cyclopentenolone.

In view of the fact that the unwanted byproduct is accumulated voluminously in the optical resolution process, a new process for utilizing the unwanted waste (R)-cyclopentenolone is being highly desired, in order that it is carried out in a commercial scale and for the purpose of rendering the optical resolution process commerically more feasible.

Under these circumstances, the present inventors have investigated various possible interconversion methods with respect to the optically active cyclopentenolones, and have found that nitrate ester of optically active cyclopentenolone, compound (II), is hydrolyzed with the inversion at the asymmetric center in the molecule. Further, they have found that it is very convenient and effective, as the method for effecting the inversion of optical isomer of the cyclopentenolones, to take a route of nitrating an optically active cyclopentenolone to its nitrate ester and then hydrolyzing the ester to give the configurationally inverted cyclopentenolone.

Thus, the present invention is to provide the method for producing optically active cyclopentenolones of the formula (I) by hydrolyzing a nitrate ester of an optically active cyclopentenolone of the formula (II), with the inversion of the configuration at the asymmetric center of the 4-position to obtain the configurationally inverted cyclopentenolone of the formula (I); the method for producing optically active cyclopentenolones of the formula (I) by nitrating an optically active cyclopentenolone of the formula (I) to its nitrate ester of the formula (II), and hydrolyzing the ester, with the inversion of configuration at the asymmetric center of the 4-position to obtain the configurationally inverted cyclopentenolone of the formula (I); and the nitrate ester of cyclopentenolones of the formula (II) as the new compounds; and the method for producing the same ester.

According to the method of the present invention, any desired optically active cyclopentenolone of the formula (I) can be obtained easily and efficiently from its optical antipode, via its nitrate ester of the formula (II).

Therefore, the unwanted (R)-isomer of the cyclopentenolone, or (R)-isomer-rich cyclopentenolone, as mentioned above, is not necessarily needed to be converted to the racemate through racemization, but can be directly and efficiently converted to the useful (S)-isomer of the cyclopentenolone, or (S)-isomer-rich cyclopentenolone, according to the method of the present invention. In combination with the optical resolution methods as mentioned before, this invention now renders the production of (S)-isomer of the formula (I) to be so convenient and feasible in a commercial scale.

It is to be noted that, as the starting material, the use of an optically active cyclopentenolone of the formula (I) which is rich in the (R)-isomer is preferred in view of the object of this invention.

DETAILED EXPLANATION OF THE PRODUCTION METHOD

An agent which is used in the process for nitrating an optically active cyclopentenolone as denoted by the formula (I) to its nitrate ester, may be nitric acid, a mixture of nitric acid and acetic anhydride where acetyl nitrate formed in situ by the mixing will substantially serve as the nitrating agent, nitronium tetrafluoroborate, nitronium trifluoromethanesulfonate, or N-nitrocollidinium tetrafluoroborate, for example.

There is no limitation as to an amount of the nitrating agent employed, but it may usually be at least one mole per one mole of the starting cyclopentenolone.

In this nitration, the use of a reaction solvent is not always necessary, but, as required, an inactive organic solvent may be used, for example, halogenated hydrocarbons such as dichloromethane, dichloroethane, chloroform and carbon tetrachloride; nitroalkanes such as nitromethane and nitroethane; lower aliphatic carboxylic acids such as acetic acid and propionic acid; lower aliphatic ketones such as acetone and methyl isobutyl ketone and the like.

The temperature for the nitration is usually in the range of $-40°$ C. to $+30°$ C., preferably $-30°$ C. to $+5°$ C.

The nitrate ester thus obtained may be used, without purification, for the subsequent hydrolysis as mentioned, to obtain the cyclopentenolone inverted at the asymmetric carbon. However, if desired, it may be purified by means of a column chromatography.

The hydrolysis process for the nitrate ester of optically active cyclopentenolones in this invention may be usually carried out in the range of 40° to 100° C., and the range of 70°–100° C. is preferred in view of the time for the reaction.

Further, as a neutralizing agent for the nitric acid generated during the hydrolysis, a carbonate salt of alkali earth metals may be used, for example, calcium carbonate, barium carbonate, and the like.

In this hydrolysis, an organic solvent is not always necessary, but some organic solvent missible to water may be used with water, if necessary. Such solvent is, for example, aliphatic cyclic ethers such as tetrahydrofuran and dioxane; lower aliphatic ketones such as acetone and methyl ethyl ketone; non-protonic polar solvents such as dimethylformamide and dimethylsulfoxide and the like.

A suitable buffer solution may also be used in order to keep the hydrolyzing condition constantly.

Reaction mixture after the hydrolysis as mentioned above may be concentrated, if desired, and the objective optically active cyclopentenolone can easily be obtained from the reaction mixture or the concentrate by an ordinary method, such as an extraction with an organic solvent.

The invention will more fully be described with respect to the following examples, which are, however, set forth merely for illustrative purpose, and not for limitative purpose.

In the following examples, the chemical purities were analyzed by a gas chromatography, and the ratios of (R)- and (S)-isomers were measured by high-performance liquid chromatography using a chiral strationary phase.

EXAMPLE 1

Into a mixed solution of 8 g of fuming nitric acid and 24 g of acetic anhydride, kept at a temperature of $-5°$ to 10° C., was added dropwise 6 g of (R)-4-hydroxy-3-methyl-2-(2-propynyl)-2-cyclopenten-1-one ($[\alpha]_D^{23}$; $-19.5°$ (C=1.36, in chloroform), (R)-isomer/(S)-isomer=96.7/3.3). Then, the mixture was stirred for 30 minutes at the same temperature. Thereafter, the reaction mixture was poured into 200 ml of ice water, and then subjected to a toluene extraction. The toluene layer was separated and washed with an aqueous 5% sodium hydrogencarbonate solution and then with water. The extract was dried over anhydrous magnesium sulfate and, then, concentrated to give 7.56 g of crude (R)-3-methyl-4-nitroxy-2-(2-propynyl)-2-cyclopenten-1-one.

A 1.24 g portion of this crude product was subjected to a silicagel column chromatography, using an eluent of hexane/ethyl acetate=7/3, to give 1.14 g of a purified product having the following properties.

Refractive index: $n_D^{23}=1.5183$

Specific Rotation: $[\alpha]_D^{23}$: $-103°$ (C=1.41, in chloroform)

IR spectrum (film, characteristic absorptions cm$^{-1}$): 3290, 2120, 1715, 1650, 1630, 1280.

NMR spectrum (CDCl$_3$, TMS):
2.04 ppm (t, J=3Hz, 1H);
2.26 ppm (s, 3H);
2.48 ppm (dd, J=2, 18Hz, 1H);
3.06 ppm (dd, J=6, 18Hz, 1H);
3.19 ppm (d, J=3Hz, 2H);
5.90 ppm (br.d, J=6Hz, 1H).

EXAMPLE 2

Ten grams of fuming nitric acid was slowly added dropwise at a temperatures of $-5°$ to 10° C. into 15 ml of a methylene chloride solution containing 1.50 g of (R)-4-hydroxy-3-methyl-2-(2-propynyl)-2-cyclopenten-1-one ($[\alpha]_D^{23}$: $-19.5°$ (C=1.36, in chloroform), (R)-isomer/(S)-isomer=96.7/3.3). After stirred for 2 hours at the same temperature, the reaction mixture was poured into 50 ml of ice water. The methylene chloride layer was separated, washed, dried and concentrated in the same way as in Example 1.

The resulting concentrate was purified using a silicagel column chromatography, and 0.55 g of (R)-3-methyl-4-nitroxy-2-(2-propynyl)-2-cyclopenten-1-one was obtained.

EXAMPLE 3

A mixture of 1.95 g of crude (R)-3-methyl-4-nitroxy-2-(2-propynyl)-2-cyclopenten-1-one prepared in Example 1, 1.00 g of calcium carbonate and 30 ml of water was stirred at a temperature of 80°–85° C. for 5 hours. Then the reaction mixture was cooled and filtered through celite. Thereafter, the water layer was saturated with sodium chloride and extracted with methyl isobutyl ketone. The organic layer was separated, washed with an aqueous saturated sodium chloride solution dried over anhydrous magnesium sulfate and, then, concentrated. Thus, 1.28 g of (S)-4-hydroxy-3-methyl-2-(2-propynyl)-2-cyclopenten-1-one (chemical purity: 90.1%, $[\alpha]_D^{23}$: +15.0° (C=1.06, in chloroform), (R)-isomer/(S)-isomer=11.6/88.4) was obtained.

Excepting the optical rotation, this product was identified to be completely identical with the starting material in Example 1, viz. (R)-4-hydroxy-3-methyl-2-(2-propynyl)-2-cyclopenten-1-one, with respect to spectra of IR and NMR, and the retention time in gas chromatography.

EXAMPLE 4

A mixture of 1.56 g of (R)-3-methyl-4-nitroxy-2-(2-propynyl)-2-cyclopenten-1-one obtained in Example 1, 0.15 g of calcium carbonate and 30 ml of water was stirred for 4 hours at a temperature of 85°–90° C. Thereafter, with the same operation as in Example 3, 1.01 g of (S)-4-hydroxy-3-methyl-2-(2-propynyl)-2-cyclopenten-1-one (chemical purity: 93.5%, $[\alpha]_D^{23}$: +14.2° (C=1.09, in chloroform), (R)-isomer/(S)-isomer=12.2/87.8) was obtained.

Excepting the optical rotation, the product was identified to be completely identical with the starting material in Example 1, viz. (R)-4-hydroxy-3-methyl-2-(2-propynyl)-2-cyclopenten-1-one with respect to spectra of IR and NMR, and the retention time in gas chromatography.

EXAMPLE 5

A mixture of 1.95 g of crude (R)-3-methyl-4-nitroxy-2-(2-propynyl)-2-cyclopenten-1-one and 30 ml of water was stirred at a temperature of 85°–90° C. for 4 hours. Thereafter, with the same operations as in Example 3, 1.35 g of (S)-4-hydroxy-3-methyl-2-(2-propynyl)-2-cyclopenten-1-one (chemical purity: 90.2%, $[\alpha]_D^{24}$: +13.1° (C=1.07, in chloroform), (R)-isomer/(S)-isomer=16.2/83.8) was obtained.

Excepting the optical rotation, the product was identified to be completely identical with the starting material in Example 1, viz. (R)-4-hydroxy-3-methyl-2-(2-propynyl)-2-cyclopenten-1-one with respect to spectra of IR and NMR, and the retention time in gas chromatography.

EXAMPLE 6

Into a mixed solution of 8 g of fuming nitric acid and 24 g of acetic anhydride, kept at a temperature of −5° to 10° C., was added dropwise 6 g of (S)-4-hydroxy-3-methyl-2-(2-propynyl)-2-cyclopenten-1-one ($[\alpha]_D^{23}$: +10.3° (C=1.17, in chloroform), (R)-isomer/(S)-isomer=15.7/84.3). Thereafter, with the same operations as in Example 1, 7.56 g of crude (S)-3-methyl-4-nitroxy-2-(2-propynyl)-2-cyclopenten-1-one was obtained.

A part of the crude product obtained above was purified in the same way as in Example 1, using a silicagel column chromatography, and the purified product having the following properties was obtained.

Refractive Index: $n_D^{24.5}$: 1.5084

Specific Rotation: $[\alpha]_D^{24.5}$: +65.4° (C=1.06, in chloroform)

IR spectrum (film, characteristic absorptions cm$^{-1}$): 1715, 1650, 1630, 1280, 915.

NMR spectrum (CDCl$_3$, TMS):
2.12 ppm (S, 3H);
2.43 ppm (dd, J=2, 18Hz, 1H);
2.96 ppm (dd, J=6, 18Hz, 1H);
3.03 ppm (d, J=6Hz, 2H);
4.80–6.20 ppm (m, 4H).

EXAMPLE 7

A mixture of 0.99 g of purified (S)-3-methyl-4-nitroxy-2-(2-propenyl)-2-cyclopenten-1-one prepared in Example 6, 0.50 g of calcium carbonate and 30 ml of water was stirred at a temperature of 85°–90° C. for 2 hours. Thereafter, with the same operations as in Example 3, 0.72 g of (R)-4-hydroxy-3-methyl-2-(2-propenyl)-2-cyclopenten-1-one (chemical purity: 94.2%, $[\alpha]_D^{24}$: −6.64° (C=1.18, in chloroform), (R)-isomer/(S)-isomer=76.2/23.8) was obtained.

Excepting the optical rotation, the product was identified to be completely identical with the starting material in Example 6, viz. (S)-4-hydroxy-3-methyl-2-(2-propenyl)-2-cyclopenten-1-one, with respect to spectra of IR and NMR, and the retention time in gas chromatography.

EXAMPLE 8

Into a mixed solution of 8 g of fuming nitric acid and 24 g of acetic anhydride, kept at a temperature of −5° to 10° C. was added dropwise 6 g of (R)-4-hydroxy-3-methyl-2-(2-propenyl)-2-cyclopenten-1-one ($[\alpha]_D^{24}$: −7.81° (C=1.07, in chloroform), (R)-isomer/(S)-isomer=77.4/22.6). Thereafter, with the same operations as in Example 1, 7.50 g of crude (R)-3-methyl-4-nitroxy-2-(2-propenyl)-2-cyclopenten-1-one was obtained.

A part of the crude product obtained above was purified in the same way as in Example 1 using a silicagel column chromatography, and a purified product having the following properties was obtained.

Refractive Index: $n_D^{24.5}$: 1.5076

Specific Rotation $[\alpha]_D^{24}$: −52.1° (C=1.40, in chloroform)

Further, NMR spectrum was identical with that of the (S)-isomer obtained in Example 6.

EXAMPLE 9

A mixture of 1.97 g of crude (R)-3-methyl-4-nitroxy-2-(2-propenyl)-2-cyclopenten-1-one prepared in Example 8, 0.20 g of calcium carbonate, 15 ml of water and 15 ml of dioxane, was stirred at a temperature of 85°–90° C. for 5 hours. Thereafter, with the same operations as in Example 3 and purification using a silicagel column chromatography (eluent: hexane/ethyl acetate=6/4), 0.57 g of (S)-4-hydroxy-3-methyl-2-(2-propenyl)-2-cyclopenten-1-one (chemical purity: 93.9%, $[\alpha]_D^{24}$: +3.80° (C=1.23, in chloroform), (R)-isomer/(S)-isomer=35.3/64.7) was obtained.

Excepting the optical rotation, the product was identified to be completely identical with the starting material in Example 8, viz. (R)-4-hydroxy-3-methyl-2-(2-propenyl)-2-cyclopenten-1-one, with respect to spectra of IR and NMR, and the retention time in gas chromatography.

EXAMPLE 10

Into a mixed solution of 5.5 g of fuming nitric acid and 22 g of acetic anhydride, kept at a temperature of −5° to 10° C., was added dropwise 4 g of (R)-4-hydroxy-3-methyl-2-(2-propenyl)-2-cyclopenten-1-one ($[\alpha]_D^{25}$: −14.9° (C=1.19, in chloroform), (R)-isomer/(S)-isomer=99.2/0.8). Thereafter, with the same operations as in Example 1, 5.02 g of crude (R)-3-methyl-4-nitroxy-2-(2-propenyl)-2-cyclopenten-1-one was obtained.

A part of the crude product obtained above was purified in the same way as in Example 1, using a silicagel column chromatography, and a purified product having the following properties was obtained.

Refractive Index: $n_D^{24.5}$: 1.5068

Specific Rotation $[\alpha]_D^{25}$: −94.7° (C=1.20, in chloroform)

Further, NMR spectrum thereof was proved to be identical with the (S)-isomer obtained in Example 6.

EXAMPLE 11

A mixture of 1.97 g of (R)-3-methyl-4-nitroxy-2-(2-propenyl)-2-cyclopenten-1-one prepared in Example 10, 0.20 g of calcium carbonate and 30 ml of water was stirred at 85°–90° C. for 3 hours. Thereafter, with the same operations as in Example 3, 1.20 g of (S)-4-hydroxy-3-methyl-2-(2-propenyl)-2-cyclopenten-1-one (chemical purity: 93.6%, $[\alpha]_D^{24}$: +11.2° (C=1.23, in chloroform), (R)-isomer/(S)-isomer=14.8/85.2) was obtained.

Excepting the optical rotation, the product was identified to be completely identical with the starting material in Example 10, viz, (R)-4-hydroxy-3-methyl-2-(2-propenyl)-2-cyclopenten-1-one, with respect to spectra of IR and NMR, and the retention time in gas chromatography.

We claim:

1. A method for producing optically active cyclopentenolones having the formula (I),

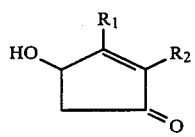

wherein $R_1$ is a hydrogen atom or a $C_1$–$C_3$ alkyl group, and $R_2$ is a $C_1$–$C_6$ alkyl, $C_2$–$C_6$ alkenyl or $C_2$–$C_6$ alkynyl group, which comprises hydrolyzing nitrate ester of an optically active cyclopentenolone of the formula (II),

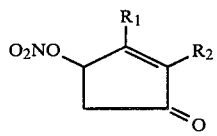

wherein $R_1$ and $R_2$ are the same as defined above, in a neutral or acidic medium, with an inversion of configuration at the asymmetric center of the 4-position to obtain the configurationally inverted cyclopentenolone of the formula (I).

2. A method according to claim 1, wherein the hydrolysis of the nitrate ester is effected in the presence of an alkali earth metal carbonate.

3. A method according to claim 1 or 2, wherein $R_1$ is methyl group, and $R_2$ is propenyl or propynyl group.

4. A method for producing optically active cyclopentenolones having the formula (I),

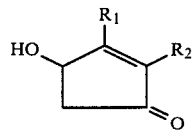

wherein $R_1$ is a hydrogen atom or a $C_1$–$C_3$ alkyl group, and $R_2$ is a $C_1$–$C_6$ alkyl, $C_2$–$C_6$ alkenyl or $C_2$–$C_6$ alkynyl group, which comprises nitrating an optically active cyclopentenolone of the formula (I) to produce its nitrate ester of the formula (II),

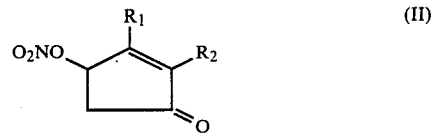

wherein $R_1$ and $R_2$ are the same as defined above, and hydrolyzing the nitrate ester in a neutral or acidic medium, with an inversion of configuration at the asymmetric center of the 4-position to obtain the configurationally inverted cyclopentenolone of the formula (I).

5. A method according to claim 4, wherein the nitrating agent is nitric acid, a mixture of nitric acid and acetic anhydride, nitronium tetrafluoroborate, nitronium trifluoromethanesulfonate or N-nitrocollidinium tetrafluoroborate.

6. A method according to claim 4 or 5, wherein the hydrolysis of the nitrate ester is effected in the presence of an alkali earth metal carbonate.

7. A method according to claim 4, 5 or 6, wherein $R_1$ is methyl group and $R_2$ is propenyl or propynyl group.

8. A nitrate ester of an optically active cyclopentenolone of the formula (II),

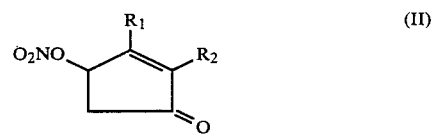

wherein $R_1$ is a hydrogen atom or a $C_1$–$C_3$ alkyl group, and $R_2$ is a $C_1$–$C_6$ alkyl, $C_2$–$C_6$ alkenyl or $C_2$–$C_6$ alkynyl group.

9. A nitrate ester according to claim 8, wherein $R_1$ is methyl group and $R_2$ is propenyl or propynyl group.

10. A method for producing nitrate ester of optically active cyclopentenolones of the formula (II),

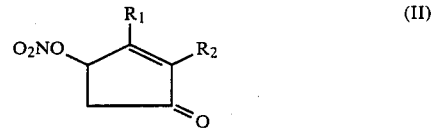

wherein $R_1$ is a hydrogen atom or a $C_1$–$C_3$ alkyl group, and $R_2$ is a $C_1$–$C_6$ alkyl, $C_2$–$C_6$ alkenyl or $C_2$–$C_6$ alkynyl group, which comprises nitrating an optically active cyclopentenolone of the formula (I),

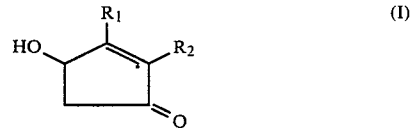

wherein $R_1$ and $R_2$ are the same as defined above, to its nitrate ester of the formula (II).

11. A method according to claim 10, wherein the nitration is conducted with nitric acid, a mixture of nitric acid and acetic anhydride, nitronium tetrafluoroborate, nitronium trifluoromethanesulfonate or N-nitrocollidinium tetrafluoroborate.

12. A method according to claim 10 or 11, wherein $R_1$ is methyl group and $R_2$ is propenyl or propynyl group.

13. A method according to any of claims 1 through 7, the objective configurationally inverted cyclopentenolone is the (S)-isomer of the cyclopentenolone or (S)-isomer-rich cyclopentenolone.

* * * * *